United States Patent [19]

Siebert

[11] Patent Number: 5,402,363

[45] Date of Patent: Mar. 28, 1995

[54] METHOD FOR ASSESSING THE RISK OF BACTERIAL CONTAMINATION IN FLUID FOODSTUFFS, BEVERAGES AND PHARMACEUTICALS

[75] Inventor: Karl J. Siebert, Geneva, N.Y.

[73] Assignee: Cornell Research Foundation, Inc., Ithaca, N.Y.

[21] Appl. No.: 23,763

[22] Filed: Feb. 26, 1993

[51] Int. Cl.$^6$ .............................................. G01N 30/04
[52] U.S. Cl. ................................... 364/554; 364/498; 364/578; 364/497
[58] Field of Search ............... 364/498, 499, 578, 496, 364/558, 554; 395/924; 73/52

[56] References Cited

U.S. PATENT DOCUMENTS

4,958,295  9/1990  Davidson et al. .................. 364/497

*Primary Examiner*—Emanuel T. Voeltz
*Assistant Examiner*—Kamini Shah
*Attorney, Agent, or Firm*—Salzman & Levy

[57] ABSTRACT

The present invention features a method of using a computer program to simulate the process of randomly selecting sample packages from a large lot of a fluid comestible or pharmaceutical, and examining a portion of the package contents for microorganisms in order to assess the risk of bacterial contamination. The computer program is used to evaluate the theoretical effects on results, such as mean, standard deviation and detection or non-detection of bacteria for various sampling choices for a particular number of samples selected from a production lot. The sampling pattern can be varied, in order to provide results related to small or large numbers of packages, with small or large volumes sampled from each. The theoretical behavior of particular organisms can be simulated in the program by applying a growth, death or stasis factor. This factor can be chosen by the practitioner based on previous testing and analyses. After completing a number of simulations and assessing the results, these results can be compared to results from actual tests. The test methodology for the particular product can then be improved by incorporating the suggested sampling procedures obtained through this comparison. Future testing can then be performed to confirm the results; still further modifications can be made of the test procedure, based on these additional tests.

17 Claims, 8 Drawing Sheets

Figure 1

Output for 100 repetitions of a specified set of conditions

List of conditions used for this simulation
LOADING
    Average load (Cells/100 ml)    4
PACKAGE ARRAY
    Package Volume (oz.)    10
    Number of Packages Simulated    10000
GROWTH, DEATH OR STASIS
    Factor (1.0 = static)    1
SAMPLING
    Packages Sampled    8
    Volume Examined    5
    Sub-samples/package    1
ITERATIONS
    No. of simulations with these conditions    100

*Figure 1a*

Pattern of packages with the indicatied numbers of organisms (count) for the package lot

```
count       bottles
  0            0
  1            1
  2            5
  3           21   *
  4           61   **
  5          143   *****
  6          281   *********
  7          474   *****************
  8          700   *************************
  9          917   *********************************
 10         1082   ***************************************
 11         1161   ******************************************
 12         1142   *****************************************
 13         1036   *************************************
 14          874   *******************************
 15          687   ************************
 16          507   ******************
 17          352   *************
 18          231   ********
 19          143   *****
 20           84   ***
 21           47   **
 22           25   *
 23           13
 24            6
 25            3
 26            1
 27            1
```

*Figure 1b*

| count | no. of packages | cumulative array |
|---|---|---|
| 0 | 27 | 0-27 |
| 1 | 162 | 28-189 |
| 2 | 477 | 190-666 |
| 3 | 938 | 667-1604 |
| 4 | 1383 | 1605-2987 |
| 5 | 1632 | 2988-4619 |
| 6 | 1605 | 4620-6224 |
| 7 | 1353 | 6225-7577 |
| 8 | 998 | 7578-8575 |
| 9 | 654 | 8576-9229 |
| 10 | 386 | 9230-9615 |
| 11 | 207 | 9616-9822 |
| 12 | 102 | 9823-9924 |
| 13 | 46 | 9925-9970 |
| 14 | 19 | 9971-9989 |
| 15 | 8 | 9990-9997 |
| 16 | 3 | 9998-10000 |
| 17 | 1 | 10001 |
| 18 | 0 | |

Figure 2

Total count in packages picked 67    In volumes examined 2

Total count in packages picked 76    In volumes examined 2

Total count in packages picked 87    In volumes examined 3

Total count in packages picked 66    In volumes examined 0

Sample total count    mean 65.25    std. dev. 11.96491
Colony total count    mean 1.04    std. dev. .9631598
Percentage of zero counts    34    non-zero 66

METHOD FOR ASSESSING THE RISK OF BACTERIAL CONTAMINATION IN FLUID FOODSTUFFS, BEVERAGES AND PHARMACEUTICALS

FIELD OF THE INVENTION

The present invention pertains to a more accurate method of determining the probability of microbial contamination in fluid comestibles and pharmaceuticals, and, more particularly, to a computer analysis and follow-up technique for more precisely assessing the risk of microbial contamination therein and for providing the best sampling procedures for a specific fluid foodstuff, beverage or pharmaceutical.

BACKGROUND OF THE INVENTION

All vendors and manufacturers of comestibles and pharmaceuticals routinely conduct sample testing of their products to determine their purity and safeness for human consumption. A part of such studies entails the microbiological examination of a number of samples taken from a given production run or lot. The number of samples and the quantity of each sample withdrawn from a production lot vary, depending upon the type of fluid that is being examined, as well as the particular procedures used by a manufacturer.

The various food industries utilize different methods and techniques in performing sample testing. A great deal of scientific analysis goes into each particular test. The testing is expensive and time-consuming; very often, it does not even provide an accurate assessment of the risk of microbial contamination. Of the many sampling techniques, none is well understood or universally respected, despite all of the scientific data and all of the advances in mathematical and statistical analysis. It is not uncommon to find that many companies use more than one method of analysis, because any one given method simply cannot be relied upon to provide an accurate picture of contamination for all products. The necessity for multiple testing bears consequences relating to the marketability of the product, since these costs, too, must be factored into the final product price.

Part of the aforementioned problem lies in the constraints that each particular foodstuff or pharmaceutical places upon the sampling methodology. Fluids that usually provide good test results are those that can be filtered through a membrane with sufficiently fine pores (so as to retain microorganisms) and which allow for large-quantity sampling (100 ml or more). The membrane is then placed on a nutrient medium, which is then incubated to provide microbial colony counts.

Fluids that contain pulp (such as fruit juice) or emulsions (such as dairy products) or those that are viscous (such as syrups and concentrates) usually block membrane filters. Direct plating techniques are used for these types of fluids. The direct plating technique, however, is typically limited by the amount of liquid that the agar of the nutrient medium can absorb. This is usually about 5 ml. Small-volume sampling is particularly troublesome when the bacterial count is low. The smaller the amount of liquid that is tested, the greater the risk of making an improper assessment of microbial contamination.

It is typical for extremely small samples (one ml) of dairy products to be plated on the agar, which makes testing problematical. In addition, when plated, the pulp particles of fruit juices may in some cases be mistaken for microbial colonies, thus giving rise to false data and improper assessment of the microbial contamination.

For organisms that tend to form chains or clumps, techniques such as those based on ATP bioluminescence tend to produce different results than do the plating methods. Plating methods count such organisms as single colonies, while ATP bioluminescence renders results based on the total number of cells in a sample.

Obviously, the many different analyses make comparisons difficult. The non-uniformities in data and procedure make risk assessments confusing and enigmatic. This is particularly true when microbial contamination is low. As mentioned, small-quantity sampling of liquids having low microbial concentrations creates an extremely high risk of inaccurately assessing what could be a potential problem.

It is now routine practice to assume that microbes in fluids are randomly dispersed throughout the total volume. A number of studies have recently found that the distribution pattern is either not significantly different from or very close to a Poisson distribution. It would, therefore, make sense to fashion a method that would utilize this distribution.

The present invention incorporates a computer program and follow-up technique for improving the microbial analysis of fluids.

The invention allows for the simulation of microbial sampling, based on a Poisson distribution, thereby improving the ability to make comparisons of various sampling strategies.

The current invention also allows the practitioner to explore the effects of organism growth, death or stasis. Current testing techniques rarely investigate these possibilities, due to the added costs and inconvenience of varying the conditions required to obtain this type of data.

The invention greatly reduces the complexity of the testing problem, leading to new insight into what procedures provide good sampling practices. For example, it has always been a standard statistical technique to increase the number of tests in order to provide greater accuracy. The present invention reflects the discovery, however, that, for low concentrations of bacterial contamination, it is preferable to analyze larger volumes of liquid, rather than a greater number of samples. In the industries utilizing this invention, an insight such as this will greatly improve future microbial assessments.

SUMMARY OF THE INVENTION

In accordance with the present invention, there are provided a computer simulation program and a follow-up procedure for assessing the risks related to microbial contamination of comestible and pharmaceutical fluids. The simulation program produces a pattern of the variation of contamination that would be expected in actual testing. The ability to provide simulations rapidly by computer calculation allows many different variables and parameters to be investigated, without requiring technicians to perform actual tests. This not only saves time and money, but also allows the practitioner to develop the best test procedures for investigating microbial contamination of a particular fluid. This, in turn, minimizes the risk associated with the sampling process. The software draws upon the intimate knowledge already gathered by the practitioners of the particular fluid under test. This knowledge is put to use by choosing realistic sampling parameters or by setting parameters relating to microbial growth, death or stasis.

The program first generates a Poisson distribution of organisms between the packages; it then generates the probability of occurrence of packages with an integer number of organisms, given a specified average organism concentration. The total number of packages is then multiplied by these probabilities, and the results are truncated. After introducing the "growth or death" factor, if used, a Cumulative Package Array is generated, beginning with the number of packages having the lowest number of organisms. This distribution pattern is used to take at least one sample aliquot from each of a selected number of sample packages. Repeated sampling can be conducted. Thereafter, a statistical summary is generated. The mean values and the standard deviations for the total organisms in all of the packages sampled and in all of the volumes examined in each replication are calculated and displayed. Thereafter, laboratory tests are conducted using a prior conventional test procedure and a new test selected from and based upon the simulation results. This follow-up procedure compares the results and provides an evaluation of the relative merits of the two schemes. Additional variations in the sampling procedures can also be made. The procedure offering the most acceptable balance between the ability to detect contamination and the expense associated with the sampling can then be chosen. In this fashion, the invention can provide a test procedure in which the risk associated with microbial contamination can be minimized.

BRIEF DESCRIPTION OF THE DRAWINGS

A complete understanding of the present invention may be obtained by reference to the accompanying drawings, when considered in conjunction with the subsequent detailed description, in which.

DESCRIPTION OF THE PREFERRED EMBODIMENT

Generally speaking, the invention features a method of using a computer program to simulate the process of randomly selecting sample packages from a large lot of a fluid comestible or pharmaceutical and examining a portion of the package contents for microorganisms. This program is used to evaluate the theoretical effects on results, such as mean, standard deviation and detection or non-detection of microbes for various sampling choices for a particular number of samples selected from a production lot. The sampling pattern can be varied, in order to provide results related to small or large numbers of packages, with small or large volumes sampled from each. The theoretical behavior of particular organisms can be simulated in the program by applying a growth, death or stasis factor. This factor can be chosen by the practitioner based on previous testing and analyses. After completing a number of simulations and assessing the results, the invention can then compare these results with results from actual tests. The test methodology for a particular product can then be improved by incorporating the suggested sampling procedures obtained through this comparison. Future testing can then be performed to confirm the results, and still further modifications can be made of the test procedure, based on these additional tests.

Figure 1:
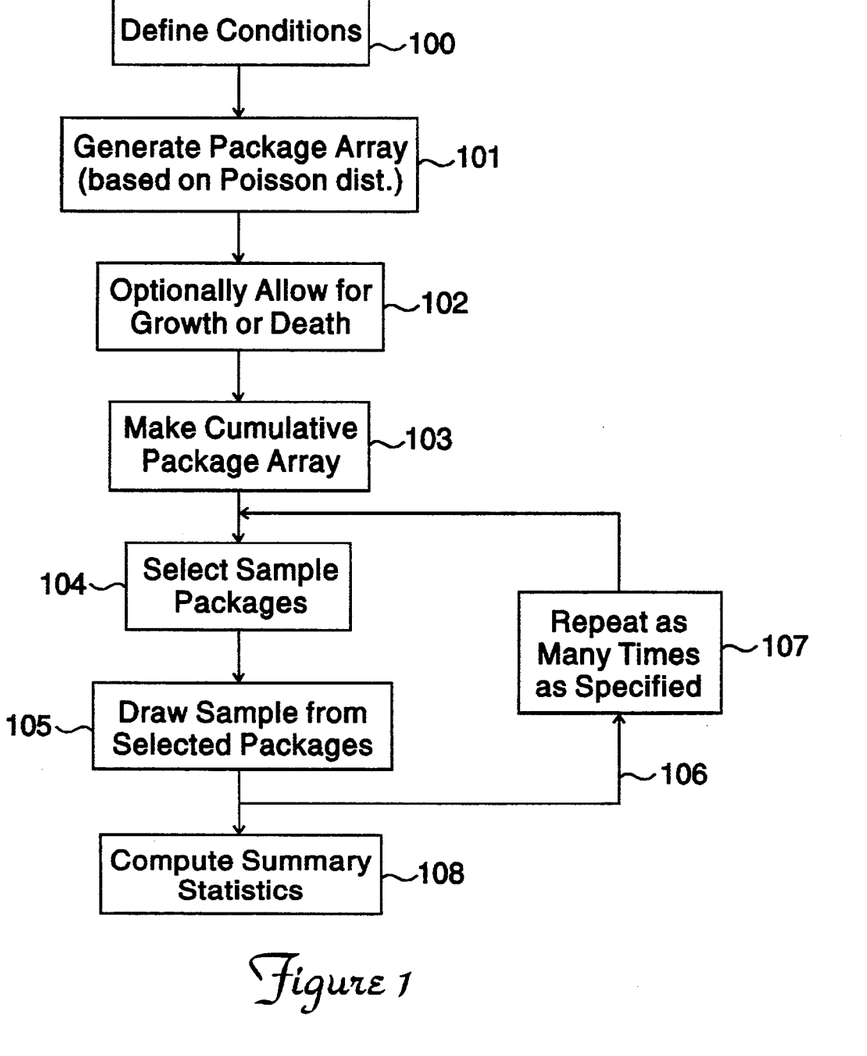
FIG. 1 depicts a flow chart of the simulation program for obtaining microbiological counts for a fluid medium in accordance with the invention.

Now referring to FIG. 1, the microbial count simulation in accordance with the invention is based on a computer program represented by the flow chart illustrated therein. The program performs a simulation of the sampling and enumeration process of a particular fluid comestible or pharmaceutical. The program does not calculate an exact answer for a given set of conditions, but, rather, produces results with the same pattern of variation expected in actual practice. The advantage of simulating variations in package selection and sampling volume is that it can be done quickly and cheaply. Furthermore, it greatly enhances the understanding of the possible risks of employing a particular methodology. Many replications can be achieved. In each simulation, however, the distribution pattern for the microorganisms is constant for a given set of conditions, including the number of packages, the average microbial load and growth assumptions. The particular packages selected for examination are chosen randomly (using a random number generator). The program is written in Microsoft QuickBasic language developed by Microsoft Corporation of Bellevue, Wash., although the algorithm could also be expressed or implemented in many other computer languages.

Figure 1A:
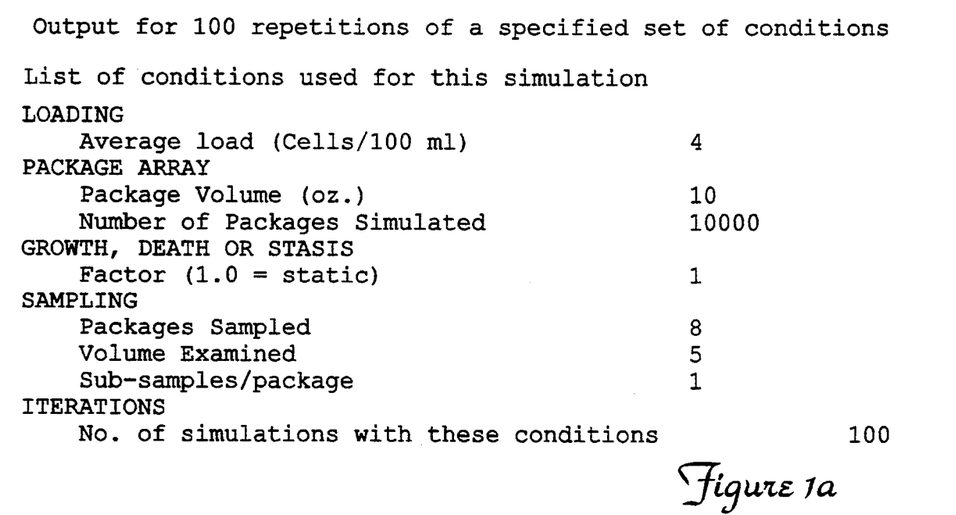
FIG. 1a shows a typical print-out of the conditions entered into the simulation program illustrated in FIG. 1.

The program first defines the conditions of the simulated test, step 100. These conditions include: (a) the average viable microorganism level expressed as the number of cells per 100 ml, (b) the package volume, (c) the number of packages in the lot, which is selected from a past or typical production run, (d) the number of packages to be sampled, (e) the volume of the liquid to be withdrawn during each examination, (f) the number of sub-samples to be taken from each package, and (g) the number of repetitions to be performed for the set of conditions (a) through (f). The set of conditions can either be read from an existing file or entered directly via the computer keyboard. A typical printout of the selected conditions is shown in FIG. 1a.

The program can simulate organism growth or death between the time that the microbial population is defined and the time that the sampling is taken. For example, this can be the time between a package exit from a pasteurizer to the time that a sample is examined. In order that this feature of the program be meaningfully utilized, it is necessary for the practitioner to have an intimate knowledge of the particular product being simulated. Previous testing is important for this aspect of the program to be successful. The growth, death or stasis of the microbial population will be explained in more detail hereinbelow with respect to step 102.

A number of options can be chosen for displaying results. These include the amount of detail printed in the report.

After the conditions are defined, step 100, the program will generate a distribution of organisms defined by the test packages, step 101. The generated package array utilizes a Poisson distribution to calculate the probability of occurrence of packages with each integer number of organisms, given a specified average organism concentration. This can be a fractional number. The total number of packages is multiplied by these probabilities and the results are truncated (to convert them to integers), in order to arrive at the number of packages with each number of organisms. For those simulations in which large numbers of organisms per package are specified, the normal distribution is used to approximate the Poisson distribution. This is a common statistical procedure, one which avoids the computational problems involved in the calculation of the Poisson distribution in such situations. The calculations for high microorganism concentrations by the Poisson formula generate some intermediate numerical results that are too small or too large to be conveniently represented in the programming language used by this invention. This is true even where double precision real numbers are employed.

Figure 1B:
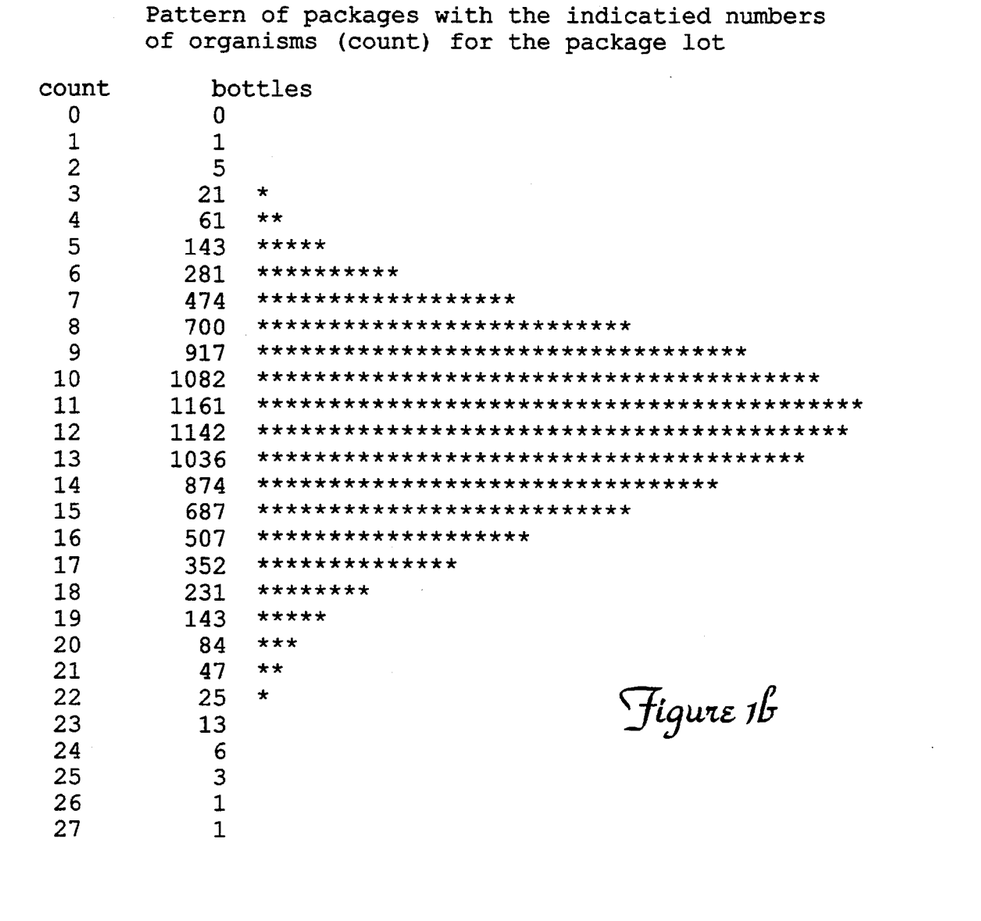
FIG. 1b depicts a distribution pattern generated in accordance with the program illustrated in FIG. 1.

The organism distribution pattern is constant for a given organism concentration, package volume and number of packages. The total number of organisms summed across packages is compared with the theoretical result calculated from the product average loading, the package volume and number of packages. The two results usually differ slightly, because one is a real number and the other equals the sum of a distribution of integer results. The distribution pattern is illustrated in FIG. 1b.

After the Package Array is generated, an allowance for growth or death may be factored into the result, step 102. This involves the specifying of a factor in the initial conditions. For example, this factor can be 0.5, indicating that half of the organisms originally present will die, or it can be 2.0, showing that twice as many organisms will be present. A factor of 1.0 can indicate no change (stasis).

The program will then generate a new distribution pattern, step 103. For example, if 825 bottles contain two organisms each, and the growth factor is 1.2, the new average for this group will be 2.4 (1.2×2.0). The number of bottles over which these organisms are now distributed remains at 825. The program realistically accounts for organism growth, since, even when these organisms grow, individual deaths still occur among the entire population. Also, some microbes remain the same (stasis), despite the increase in the average growth. Packages that initially had no microbes will have none at the later time.

Figure 2:
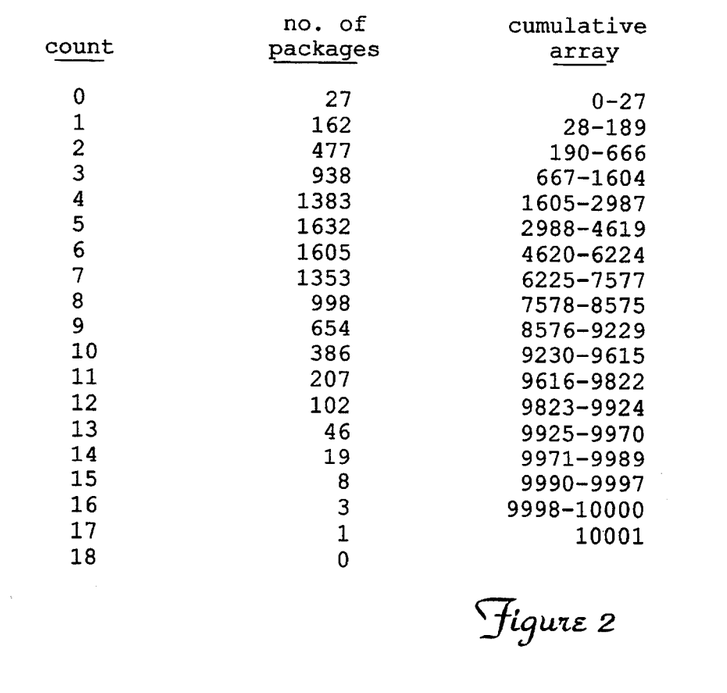
FIG. 2 shows a simulated cumulative organism distribution pattern obtained with the program, after growth factors have been calculated.

A typical distribution pattern for the generated Cumulative Package Array, step 103, listing the number of packages with each number of organisms per package (count), is shown in FIG. 2.

The program will now select a number of sample packages, step 104. A random number between 0 and 1 is generated and multiplied by the total number of packages. This is truncated to arrive at an integer. For example, if 10,000 bottles are in the array, this generates a number between 1 and 10,000. Suppose the random generated number is 0.1073; then, this is multiplied by the 10,000 bottles to yield 1,073. The program then finds that the randomly selected bottle number in the Cumulative Array which brackets 1,073 corresponds to a package with three organisms. A higher bottle number corresponds to a package with a higher organism loading, while lower numbers correspond to lower loadings. The counts in all of the selected packages are summed to arrive at the total number of organisms in all of the packages chosen.

The program then proceeds to examine a volume of each selected package, step 105. A Cumulative Array of the Poisson probabilities of occurrence of each discrete result is prepared, using the number of organisms in the chosen package, the package volume and the sample volume to define the expected result. A random number in the range of 0 through 1 is then used to index this array. This calculation usually yields the result expected from the ratio (sample volume/package volume)×selected-package count. It also yields both lower and higher results with increasingly smaller frequencies of occurrence, the farther the number diverges from the ratio.

The number of organisms and volume available are decremented, and the process repeated, if additional subsamples are to be drawn from the packages. The simulation of withdrawing aliquots from the other selected packages is also accomplished in similar fashion. The results are summed to indicate the total number of organisms in all of the packages sampled and in all of the volumes examined from this lot. The process of package selection and sampling is repeated, step 107 and program loop 106, depending on the specified number of iterations selected in the initial conditions, step 100.

Figure 3:
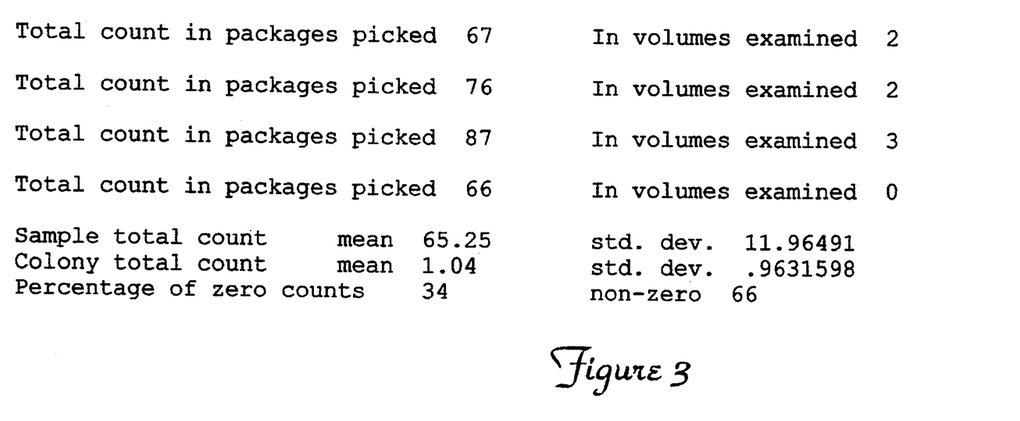
FIG. 3 illustrates a portion of a typical report and statistical summary obtained with the program of FIG. 1.

These results are then utilized by the program to provide a summary statistical report, step 108. The mean values and standard deviations for the total organisms in all of the packages sampled and in all of the volumes examined in each replication are calculated and displayed, as shown in a typical report illustrated in FIG. 3. Each line at the top of FIG. 3 indicates results from one simulation, showing a total number of organisms in all selected packages, and the total number of organisms found in all volumes examined. The bottom of FIG. 3 illustrates a statistical summary for all replications made for a set of conditions. The sample total count is for the total organisms in all packages selected. The total colony total count results are for the total organisms found in the volumes examined. The percentage of occurrence of zero and non-zero counts is also reported.

At this stage in the analysis, simulations using conditions for a standard procedure and that of a test procedure are plotted and compared. This comparison is a follow-up procedure to the program described in FIG. 1. The plots permit evaluation of the relative merits of the two schemes. Additional variations could then be made in the simulation program, and a further evaluation made. The final optimized testing procedure for the particular fluid under examination depends on the balance between the ability to detect contamination and the expense of performing the sampling. Such expense includes the cost of the sample packages consumed, the laboratory materials used and the labor required to perform the tests. The final chosen procedure itself would then be in need of testing in actual practice to confirm the results. If the new procedure proved to be superior to the old procedure, it would then become the standard for that particular product.

The microbiological count simulation computer program was used to perform a number of simulations. At least 100 replicate simulations were made for each set of conditions. The simulations were all for 10 oz (295 ml) packages, and samples were drawn from 10,000 package lots in each case. The assumptions were that no growth or death occurred between the specification of organism concentration and sampling, and that the organisms were randomly distributed among packages and within the volume of each package.

The effects of the sample volume taken for examination, the distribution of the total sample volume between packages and the numbers of packages sampled were examined at various microbial concentrations. For the sample volume study, simulations for volumes of 1, 2, 5, 10, 20, 50, 100 and 250 ml from 8- and 16-package sets were carried out for average microbial loadings of 0.1, 0.2, 0.5, 1.0, 1.5, 2.0, 2.5, 3.0, 3.5 and 4.0 organisms/100 ml. In the package number study, simulations of sampling 5 ml volumes from 1, 2, 4, 8, 16, 32, and 64 selected packages and 100 ml volumes from 1, 2, 4, 8 and 16 selected packages over the same range of loadings were performed. The distribution study examined the effects of taking a total of 16 samples of 5 ml from different numbers of selected packages; this ranged from 16 aliquots all from the same package through one aliquot from each of 16 selected packages. Another distribution study compared the results of taking 100 ml of total sample volume from different numbers of packages, ranging from 1 sample of 100 ml through combinations of 2×50 ml, 5×20 ml, 10×10 ml, 20×5 ml, 50×2 ml to 100 packages with 1 ml samples. The combinations of parameters to carry out these studies were supplied to the computer program and simulations were carried out. Results for mean count found, standard deviation and percent zero results (the incidence of non-detection of contamination) were noted in each case.

The study design described above was intended to provide a systematic examination of what could be expected under a variety of conditions. It was also intended to evaluate the influence of each factor on the mean result, precision and risk.

The first variable examined was sample volume. For each of a number of average microbial loadings in the range 0.1–4.0 microorganisms/100 ml sample, simulations were performed for sets of 8 and 16 selected packages and a number of sample volumes in the range 1 ml through 250 ml. The data are shown below in Tables 1 and 2, and can be graphed in a number of ways.

TABLE 1*

| Means for 100 Simulations of Indicated Conditions | | | | | | | | |
|---|---|---|---|---|---|---|---|---|
| | Sample Volume (ml) | | | | | | | |
| Load | 1 | 2 | 5 | 10 | 20 | 50 | 100 | 250 |
| 0.10 | 0.01 | 0.03 | 0.10 | 0.17 | 0.39 | 0.87 | 1.60 | 3.67 |
| 0.20 | 0.02 | 0.08 | 0.13 | 0.41 | 0.56 | 1.43 | 2.95 | 7.99 |
| 0.50 | 0.10 | 0.12 | 0.37 | 0.72 | 1.44 | 3.77 | 8.29 | 19.19 |
| 1.00 | 0.22 | 0.35 | 0.89 | 1.86 | 3.09 | 7.98 | 15.78 | 39.98 |
| 1.50 | 0.32 | 0.52 | 1.18 | 2.25 | 4.49 | 12.21 | 24.34 | 60.41 |
| 2.00 | 0.27 | 0.60 | 1.36 | 3.17 | 6.34 | 16.17 | 31.86 | 80.09 |
| 2.50 | 0.46 | 0.91 | 1.98 | 4.21 | 7.94 | 20.20 | 39.82 | 100.66 |
| 3.00 | 0.56 | 0.91 | 2.23 | 4.89 | 9.53 | 24.29 | 48.15 | 119.99 |
| 3.50 | 0.45 | 1.03 | 2.83 | 5.78 | 11.23 | 27.78 | 53.38 | 140.30 |
| 4.00 | 0.61 | 1.23 | 3.01 | 6.60 | 12.45 | 32.96 | 64.62 | 159.38 |

| Standard Deviations for 100 Simulations of Indicated Conditions | | | | | | | | |
|---|---|---|---|---|---|---|---|---|
| | Sample Volume (ml) | | | | | | | |
| Load | 1 | 2 | 5 | 10 | 20 | 50 | 100 | 250 |
| 0.10 | 0.099 | 0.171 | 0.333 | 0.428 | 0.618 | 0.971 | 1.393 | 2.084 |
| 0.20 | 0.141 | 0.307 | 0.367 | 0.712 | 0.729 | 1.265 | 1.904 | 2.904 |
| 0.50 | 0.302 | 0.356 | 0.614 | 0.805 | 1.225 | 2.242 | 3.859 | 4.287 |
| 1.00 | 0.524 | 0.609 | 0.973 | 1.333 | 1.870 | 3.357 | 4.113 | 6.168 |
| 1.50 | 0.548 | 0.717 | 1.158 | 1.666 | 2.067 | 3.777 | 5.562 | 8.034 |
| 2.00 | 0.548 | 0.791 | 1.330 | 1.870 | 2.724 | 4.233 | 6.883 | 7.810 |
| 2.50 | 0.593 | 0.965 | 1.206 | 2.240 | 2.752 | 5.538 | 7.770 | 10.268 |
| 3.00 | 0.756 | 1.045 | 1.496 | 2.326 | 3.401 | 5.734 | 8.539 | 11.288 |
| 3.50 | 0.642 | 1.039 | 1.682 | 2.549 | 3.499 | 6.475 | 7.858 | 11.400 |
| 4.00 | 0.764 | 1.024 | 1.667 | 2.704 | 3.735 | 5.666 | 9.153 | 13.442 |

*Results for Simulated Examinations of 16 Sample Sets for Indicated Microbial Loadings (cells/1000 ml) and Sample Volumes

| Percent of 100 Simulations With Zero Results for All Samples | | | | | | | | |
|---|---|---|---|---|---|---|---|---|
| | Sample Volume (ml) | | | | | | | |
| Load | 1 | 2 | 5 | 10 | 20 | 50 | 100 | 250 |
| 0.10 | 99 | 97 | 91 | 85 | 68 | 47 | 25 | 10 |

TABLE 1*-continued

| 0.20 | 98 | 93 | 88 | 70 | 57 | 26 | 6 | 0 |
| 0.50 | 90 | 89 | 69 | 45 | 22 | 5 | 0 | 0 |
| 1.00 | 82 | 72 | 43 | 14 | 4 | 0 | 0 | 0 |
| 1.50 | 72 | 60 | 37 | 13 | 1 | 0 | 0 | 0 |
| 2.00 | 77 | 54 | 33 | 6 | 0 | 0 | 0 | 0 |
| 2.50 | 59 | 41 | 10 | 3 | 0 | 0 | 0 | 0 |
| 3.00 | 56 | 44 | 12 | 2 | 0 | 0 | 0 | 0 |
| 3.50 | 63 | 39 | 3 | 1 | 0 | 0 | 0 | 0 |
| 4.00 | 53 | 26 | 2 | 0 | 0 | 0 | 0 | 0 |

*Results for Simulated Examinations of 16 Sample Sets for Indicated Microbial Loadings (cells/100 ml) and Sample Volumes

TABLE 2**

Means for 100 Simulations of Indicated Conditions

| Load | Sample Volume (ml) | | | | | | | |
|---|---|---|---|---|---|---|---|---|
| | 1 | 2 | 5 | 10 | 20 | 50 | 100 | 250 |
| 0.10 | 0.00 | 0.00 | 0.05 | 0.13 | 0.16 | 0.45 | 0.75 | 1.81 |
| 0.20 | 0.02 | 0.01 | 0.08 | 0.14 | 0.20 | 0.95 | 1.54 | 4.30 |
| 0.50 | 0.01 | 0.13 | 0.16 | 0.36 | 0.73 | 1.94 | 3.88 | 9.77 |
| 1.00 | 0.05 | 0.17 | 0.37 | 0.72 | 1.67 | 4.30 | 7.81 | 19.91 |
| 1.50 | 0.14 | 0.25 | 0.70 | 1.17 | 2.32 | 6.13 | 12.25 | 29.86 |
| 2.00 | 0.19 | 0.29 | 0.75 | 1.36 | 3.09 | 7.52 | 15.61 | 39.08 |
| 2.50 | 0.31 | 0.47 | 0.73 | 2.11 | 3.92 | 10.14 | 19.99 | 50.78 |
| 3.00 | 0.32 | 0.44 | 1.41 | 2.27 | 4.96 | 11.36 | 23.51 | 60.50 |
| 3.50 | 0.30 | 0.59 | 1.34 | 2.57 | 5.43 | 14.76 | 28.08 | 69.89 |
| 4.00 | 0.31 | 0.61 | 1.68 | 3.21 | 6.35 | 15.82 | 31.38 | 78.88 |

**Results for Simulated Examinations of 8 Sample Sets for Indicated Microbial Loadings (cells/100 ml) and Sample Volumes

Standard Deviations for 100 Simulations of Indicated Conditions

| Load | Sample Volume (ml) | | | | | | | |
|---|---|---|---|---|---|---|---|---|
| | 1 | 2 | 5 | 10 | 20 | 50 | 100 | 250 |
| 0.10 | 0.000 | 0.000 | 0.219 | 0.367 | 0.443 | 0.730 | 0.978 | 1.398 |
| 0.20 | 0.141 | 0.099 | 0.273 | 0.349 | 0.449 | 1.019 | 1.374 | 2.130 |
| 0.50 | 0.099 | 0.367 | 0.368 | 0.595 | 0.897 | 1.462 | 2.375 | 2.920 |
| 1.00 | 0.219 | 0.428 | 0.630 | 0.866 | 1.198 | 2.272 | 3.678 | 4.551 |
| 1.50 | 0.377 | 0.500 | 0.810 | 1.101 | 1.663 | 2.646 | 4.098 | 5.784 |
| 2.00 | 0.465 | 0.556 | 1.019 | 1.219 | 1.804 | 3.380 | 4.077 | 6.462 |
| 2.50 | 0.526 | 0.688 | 0.886 | 1.421 | 2.097 | 3.473 | 5.697 | 7.437 |
| 3.00 | 0.548 | 0.671 | 1.198 | 1.413 | 2.283 | 3.656 | 5.866 | 7.324 |
| 3.50 | 0.522 | 0.805 | 1.320 | 1.533 | 2.836 | 4.245 | 5.937 | 9.305 |
| 4.00 | 0.581 | 0.852 | 1.278 | 1.966 | 2.488 | 4.115 | 6.987 | 8.834 |

Percent of 100 Simulations With Zero Results for All Samples

| Load | Sample Volume (ml) | | | | | | | |
|---|---|---|---|---|---|---|---|---|
| | 1 | 2 | 5 | 10 | 20 | 50 | 100 | 250 |
| 0.10 | 100 | 100 | 95 | 88 | 86 | 67 | 51 | 16 |
| 0.20 | 98 | 99 | 92 | 86 | 82 | 42 | 25 | 1 |
| 0.50 | 99 | 88 | 84 | 69 | 50 | 14 | 5 | 0 |
| 1.00 | 95 | 85 | 70 | 49 | 14 | 1 | 0 | 0 |
| 1.50 | 87 | 77 | 49 | 35 | 9 | 0 | 0 | 0 |
| 2.00 | 84 | 76 | 55 | 24 | 2 | 0 | 0 | 0 |
| 2.50 | 72 | 63 | 46 | 9 | 2 | 0 | 0 | 0 |
| 3.00 | 72 | 65 | 24 | 10 | 0 | 0 | 0 | 0 |
| 3.50 | 73 | 55 | 27 | 7 | 1 | 0 | 0 | 0 |
| 4.00 | 74 | 59 | 16 | 5 | 1 | 0 | 0 | 0 |

Figure 4:
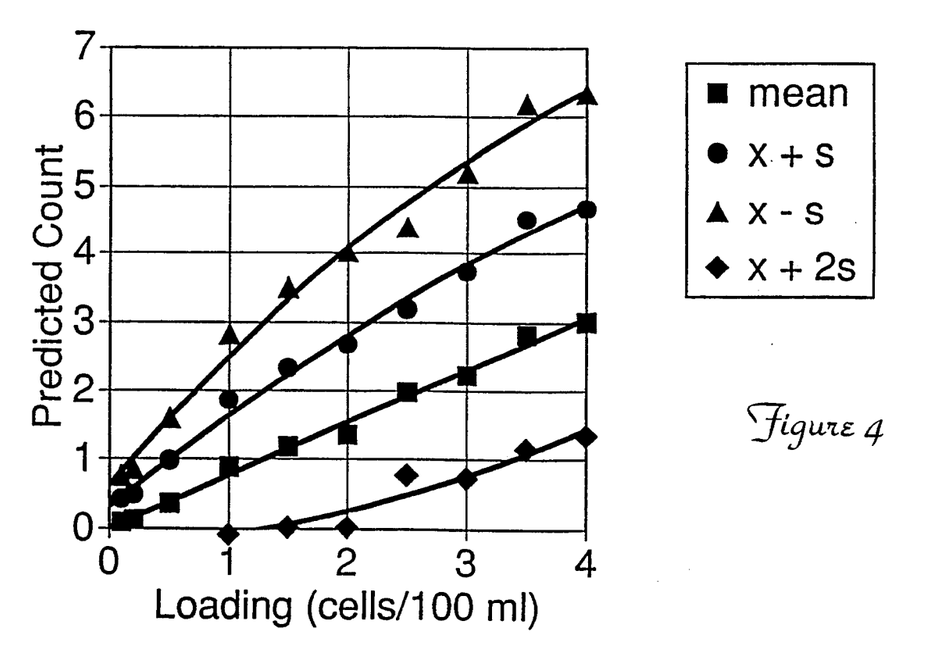
FIG. 4 depicts a graph, featuring results from one hundred replicate simulations in which a 5 ml sample from each of sixteen selected packages was examined; the mean and mean plus and minus one or two standard deviations are shown thereon.
Figure 5:
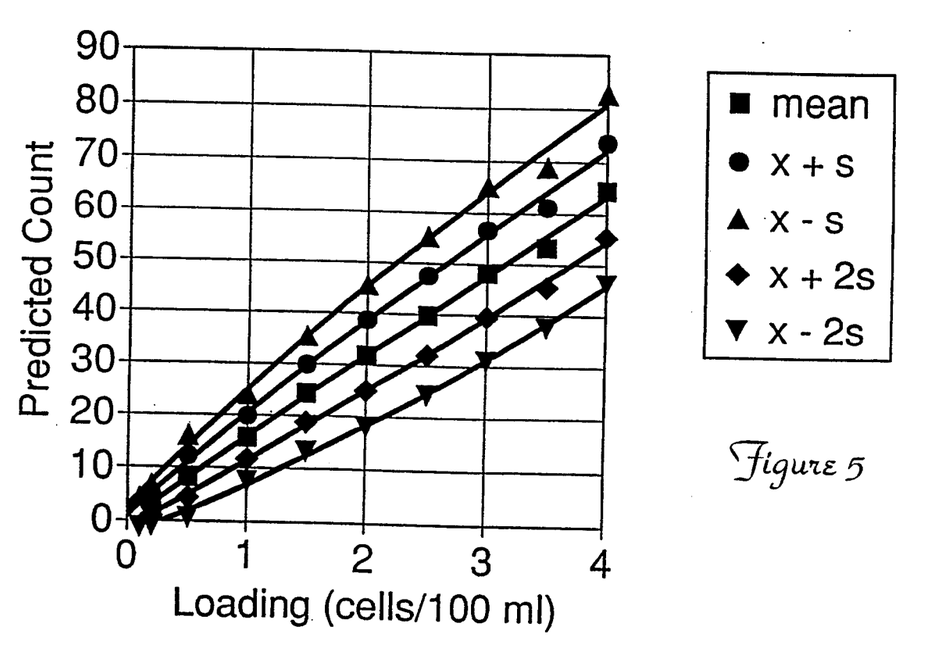
FIG. 5 shows a graph featuring results from one hundred replicate simulations in which a 100 ml sample from each of sixteen selected packages was examined. The mean and mean plus and minus one or two standard deviations are illustrated thereon.

**Results for Simulated Examinations of 8 Sample Sets for Indicated Microbial Loadings (cells/100 ml) and Sample Volumes FIGS. 4 and 5 show the mean predicted total count results (the sum of all colonies seen on all plates) from one hundred replicate simulations, and the variation depicted as the mean plus or minus 1 or 2 standard deviations for the 5 ml and 100 ml sample sizes, respectively, from sixteen packages. It is quite apparent that the variation expressed as the mean result plus or minus one or two standard deviations, is relatively large with the smaller sample volumes. For one ml samples, the standard deviation is as large as the mean result (see Table 1). The standard deviation becomes smaller relative to the mean as the sample size increases. For any single Poisson distribution, the variance is approximately equal to the expected result. This would be consistent with a standard deviation that decreases as the mean increases. The results from the simulation study are in general agreement with a variance/mean ratio of 1.0.

Figure 6:
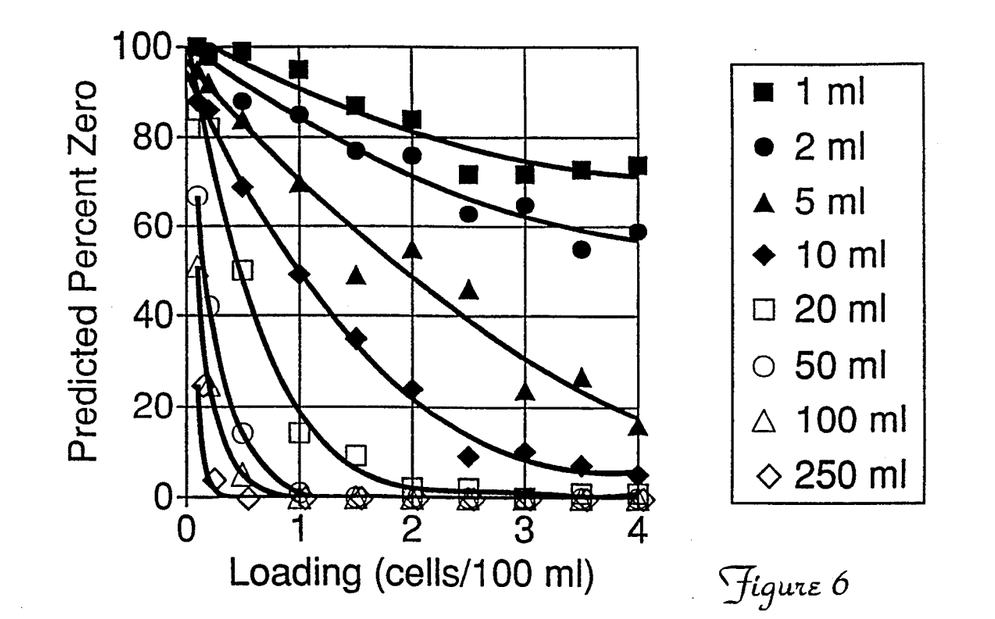
FIG. 6 depicts a graph of the results from one hundred replicate simulations in which samples of the indicated volumes were taken from each of eight selected packages.
Figure 7:
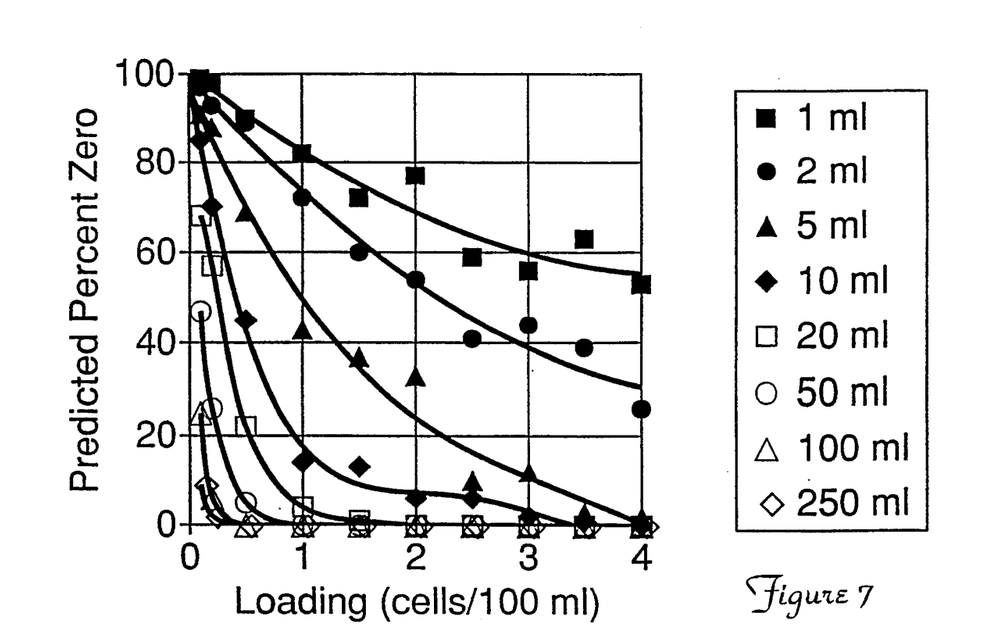
FIG. 7 illustrates a graph of the results from one hundred replicate simulations in which samples of the indicated volumes were taken from each of sixteen selected packages.

Perhaps the simplest expression of the degree of risk implicit in these results is the frequency of occurrence of zero results in all the samples in a set (designated here the predicted percent zero). This was plotted for selections of 8 and of 16 samples, as illustrated in FIGS. 6 and 7.

At the 0.1 cell/100 ml level (roughly equivalent to an average of one cell in every third 10 oz. package), 5 ml platings of 16 packages would yield no counts approximately 90% of the time. The likelihood of finding no counts at this organism loading falls to about 25% with 100 ml samples. With average loadings of 0.2 cells/100 ml, examination of 100 ml platings from 16 packages would nearly always yield some counts. With 5 ml samples, it can be seen that a zero result for all 16 plates could very easily occur even with rather high loadings. For reference, a loading of 0.33 cells/100 ml is approximately one organism per 10 oz. (295 ml) package, while 1 cell/100 ml is about three organisms per package. Clearly the volume of sample examined has a very large effect on the likelihood of finding microbial contamination. Sample volumes of 1 ml or 2 ml, even when taken from 16 packages, can easily fail to detect quite high organism concentrations.

Figure 8:
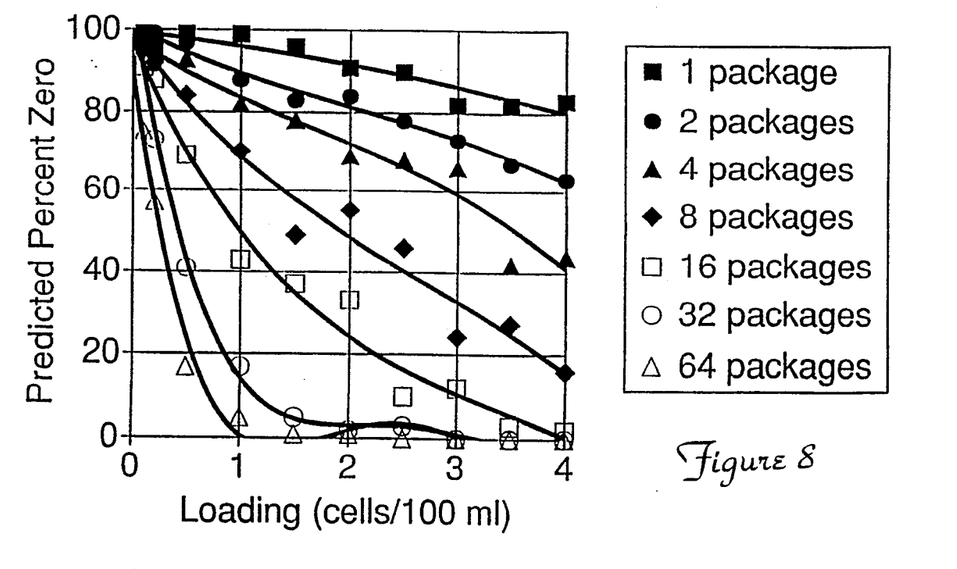
FIG. 8 shows a graph of the results from one hundred replicate simulations in which one 5 ml sample was taken from the indicated number of selected packages.
Figure 9:
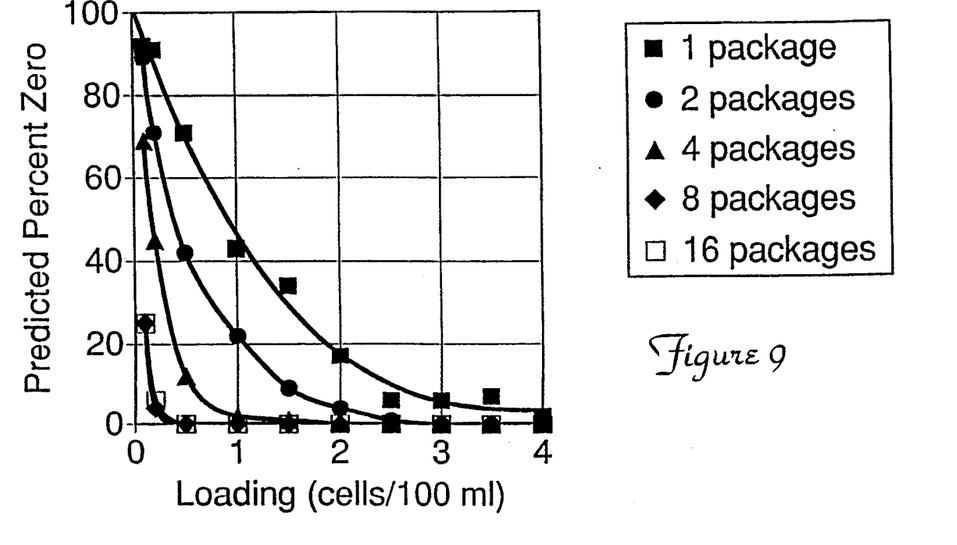
FIG. 9 depicts a graph of the results from one hundred replicate simulations in which one 100 ml sample was taken from the indicated number of selected packages.

The effect of the number of packages examined with 5 ml and 100 ml platings was also investigated. The results are shown in FIGS. 8 and 9. With 5 ml samples, examination of a single package offers very little likelihood of detecting even the highest levels of contamination; 16 packages are needed to have close to a 50% chance of detecting 1 cell/100 ml (about 3 cells/10 oz. package). It is clear that a zero result is no assurance of sterility. With 64 samples, an average loading of 1 cell/100 ml would be detected over 90% of the time.

Referring to FIG. 9, it is clear that, with platings that correspond to 100 ml of sample, fewer samples are needed to achieve equal or better detection efficiency. It can be seen that a single 100 ml sample should be better than 16 samples of 5 ml each. This is logical, since 16 samples of 5 ml each contains a total of only 80 ml. This was confirmed by comparing results for a single 100 ml sample with 20 samples of 5 ml (data not shown); the results were very similar in mean and precision. In this sample volume range, the results appear to be dependent mainly on the total sample volume examined rather than the number of samples if the random distribution assumption holds. With larger volume samples, the benefit of increasing the number of samples eventually appears to diminish. (Compare results for 8 and 16 packages in FIG. 9.)

Figure 10:
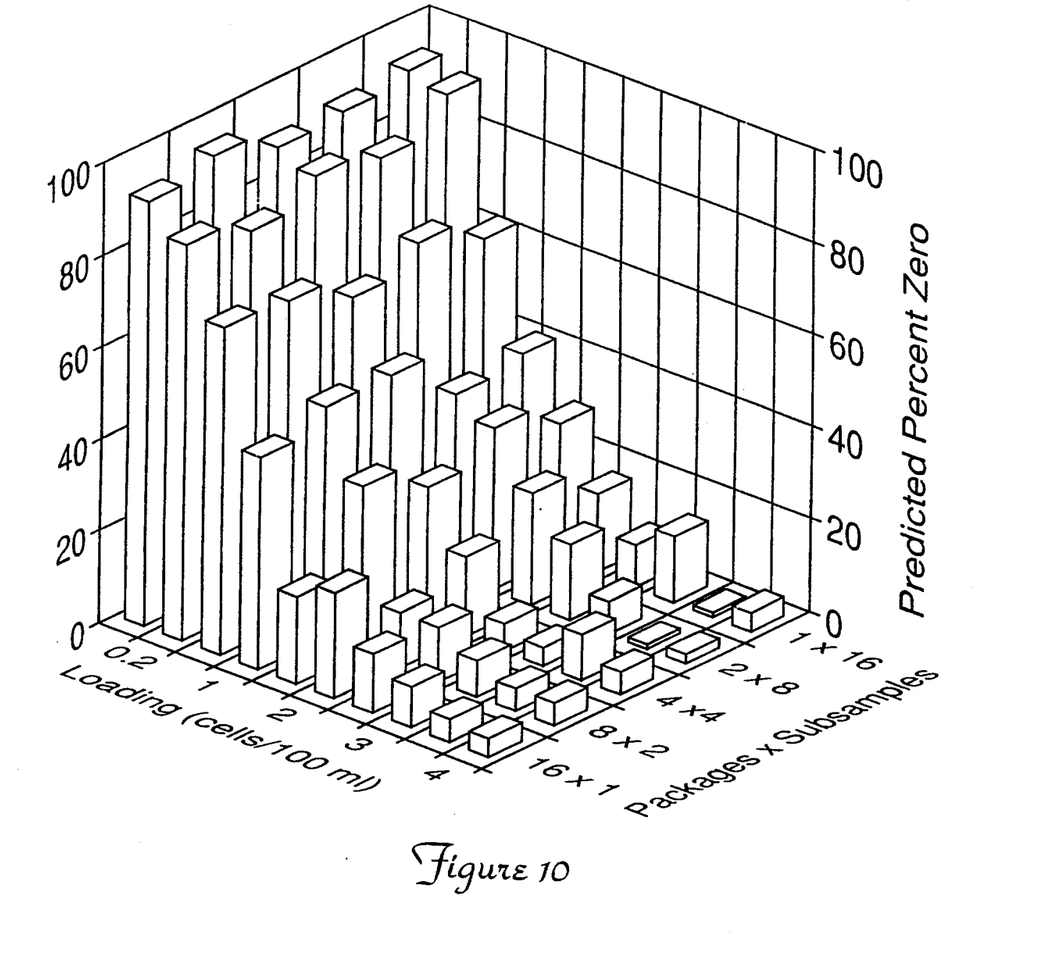
FIG. 10 illustrates a bar graph distribution of the results of one hundred replicate simulations in which a total of sixteen samples of 5 ml was taken from 1, 2, 4, 8 or 16 packages.

Simulations in which the same total sample volume was distributed in several ways were carried out. In one case, 16 samples of 5 ml each were taken from 1, 2, 4, 8 or 16 packages. The results are shown in FIG. 10 and indicate virtually no effect of the sampling pattern on detection efficiency.

Figure 11:
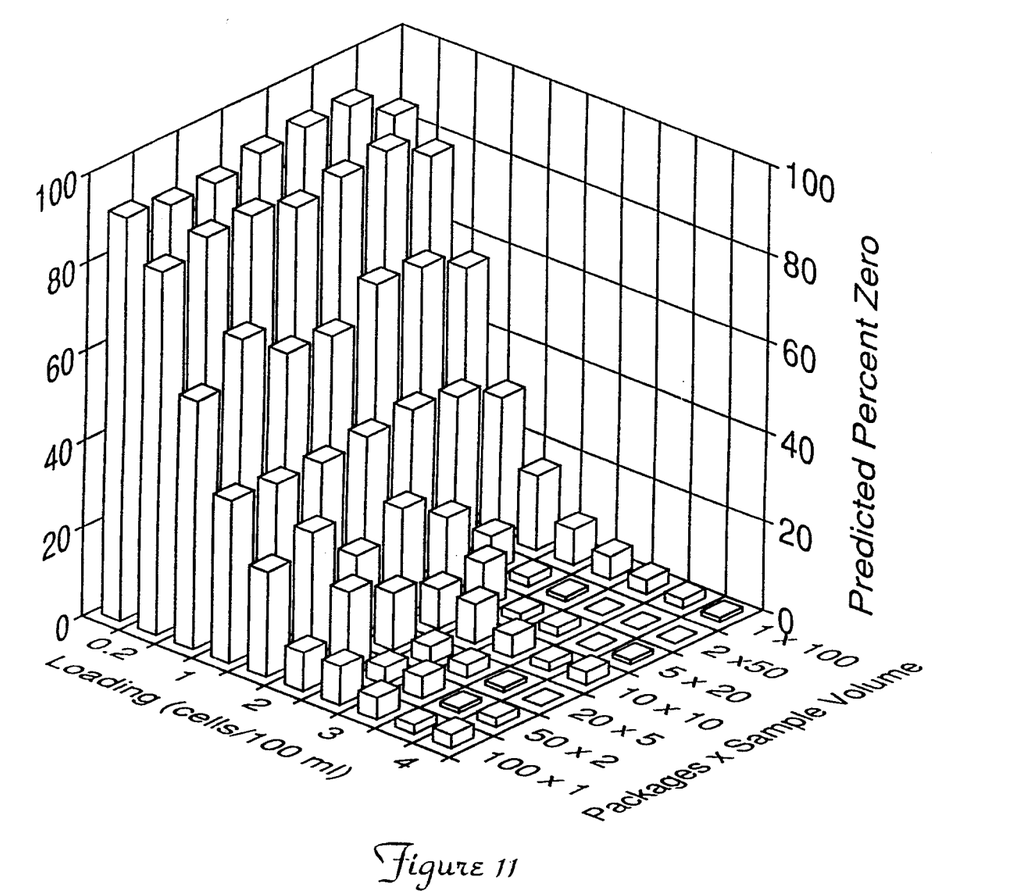
FIG. 11 depicts a bar graph distribution of the results of one hundred replicate simulations in which a total of 100 ml was taken from 1, 2, 5, 10, 20, 50 or 100 packages.

A comparison of predicted frequency of finding no counts, in which different numbers of packages each examining a total volume of 100 ml, were simulated as shown in FIG. 11. Once again, the results were similar in mean, standard deviation and percentage of zero counts.

Clearly the total volume examined is the factor with the strongest influence on results. Changing the distribution of the sampled volume between packages has little effect. For a given volume examined per package, the number of packages sampled appears to exert its effect mainly through its influence on the total volume sampled. However, with the largest examined volumes, the benefit of sampling larger numbers of packages declines. For most practical samples, the total volume examined will be the important factor, provided that the counts are randomly distributed over the entire package population. This has important implications both for the choice of sampling pattern employed and for the cost of sampling.

The principle that the number of packages examined should be a function of the size of the lot is manifest when the organism distribution pattern is expected to deviate from a random distribution. Otherwise the total volume examined should be the key factor. For processes involving aseptic filling, the assumption that organisms are randomly distributed across packages is more likely to be correct early in a filling run when the equipment should be cleaner. Some time after cleaning, certain spouts of a multi-spout filler may become infected. This could lead to a less random distribution of organisms across packages. Such divergences from a random distribution pattern are thus likely to increase with the length of a filling operation or the interval between filler cleanings. Where tunnel pasteurizers are employed following filling, differences between packages caused by contamination of individual filler spouts are likely to be small, particularly for low or modest levels of contamination.

Increasing the volume basis of the sample applied to a plate has a great effect on the likelihood of detecting organisms; it also improves precision. Sample permitting, the largest practical volume that can be examined should be used. It is of considerable interest to develop approaches to examine larger sample volumes; procedures that increase the volume basis for difficult samples should be particularly useful.

The number of packages examined influences results, but the effect is not as strong as that of the sample volume examined. The amount of additional work required to examine enough additional samples to improve the confidence of the results appears to be great, compared to the improvement that could be gained through increasing the volume of each sample. In some cases increasing the number of samples examined may be the only feasible option to reduce risk or improve the assessment.

If organisms are distributed randomly across all packages, varying the number of packages or sub-samples from which the same total sample volume is drawn would not be expected to change the pattern of results.

It is clearly apparent from the above that if the random distribution assumption holds, the preferred sampling strategy, where the nature of the sample permits, is to take fewer samples of larger volumes. This is cost effective in two ways: it reduces product loss due to the destructive nature of microbial sampling; and it reduces the labor cost that is usually a function of the number of samples.

Substitution of various combinations of sampling approaches, such as taking fewer samples of larger volume, must be tested on a case-by-case basis. The count simulation program makes theoretical comparisons of this sort readily possible.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed is:

1. A method of simulating a process of randomly selecting sample packages from a large lot of a fluid, and examining a portion of each selected sample package for microorganisms, and thereafter comparing the simulated process with a prior test procedure to determine a better test procedure for assessing a risk of contamination in said fluid, the method comprising the steps of:

a) defining a number of test conditions related to a fluid being tested;
b) generating a Poisson distribution of organisms between packages of said fluid, and then
c) generating a probability of occurrence of packages with an integer number of organisms, given a specified average organism concentration;
d) multiplying a total number of packages by this probability;
e) simulating a taking of at least one sample aliquot from each selected sample package of a group of sample packages;
f) thereafter, generating a statistical summary including mean values for total organisms in all of the packages sampled and in all volumes examined;
g) conducting a number of actual tests using a prior test procedure, including a measurement of microorganisms in actual samples, and using the simulated process in accordance with steps (a) through (f); and
h) comparing results between the prior test procedure and the simulated process to evaluate these tests.

2. The method in accordance with claim 1, wherein the conditions defined in step (a) include: (i) average viable microorganism level, expressed as a number of cells per unit volume, (ii) a package volume, (iii) a number of packages in a lot, which is selected from a past or typical production run, (iv) a number of packages to be sampled, (v) a volume of the liquid to be withdrawn during each examination, and (vi) a number of repetitions to be performed for the conditions (i) through (v).

3. The method in accordance with claim 2, wherein the conditions defined in step (a) further include the step of: (vii) taking a number of sub-samples from each package.

4. The method in accordance with claim 1, wherein the fluid comprises a comestible.

5. The method in accordance with claim 1, wherein the fluid comprises a pharmaceutical.

6. A method of simulating a process of randomly selecting sample packages from a large lot of a fluid, and examining a portion of each selected sample package for microorganisms, and thereafter comparing the simulated process with a prior test procedure to determine a better test procedure for assessing a risk of contamination in said fluid, the method comprising the steps of:
a) generating a Poisson distribution of organisms between packages of a fluid, and then
b) generating a probability of occurrence of packages with an integer number of organisms, given a specified average organism concentration;
c) simulating a taking of at least one sample aliquot from each selected sample package of a group of sample packages;
d) thereafter, generating a statistical summary including mean values for total organisms in all packages sampled and all volumes examined;
e) conducting a number of actual tests using a prior test procedure, including a measurement of microorganisms in actual samples, and using the simulated process in accordance with steps (a) through (d); and
f) comparing results between the prior test procedure and the simulated process to evaluate these tests.

7. The method in accordance with claim 6, wherein the conditions defined in step (a) include: (i) average viable microorganism level, expressed as a number of cells per unit volume, (ii) a package volume, (iii) a number of packages in a lot, which is selected from a past or typical production run, (iv) a number of packages to be sampled, (v) a volume of the liquid to be withdrawn during each examination, and (vi) a number of repetitions to be performed for the conditions (i) through (v).

8. The method in accordance with claim 7, wherein the conditions defined in step (a) further include the step of: (vii) taking a number of sub-samples from each package.

9. The method in accordance with claim 6, wherein the fluid comprises a comestible.

10. The method in accordance with claim 6, wherein the fluid comprises a pharmaceutical.

11. The method in accordance with claim 6, further comprising the step of:
g) introducing a growth, death or stasis factor, and then generating a cumulative package array distribution.

12. A method of testing a fluid for microorganisms by a simulated process of randomly selecting simulated sample packages from a large lot of said fluid, generating a Poisson distribution for organisms in said simulated sample packages, examining a portion of each selected simulated sample package for microorganisms and generating a statistical report, performing actual fluid tests based on said simulated process, including a measurement of microorganisms in said fluid, and thereafter comparing said actual fluid tests performed, using the simulated process and a prior test procedure to determine a better test procedure for assessing the risk of contamination in said fluid.

13. The method in accordance with claim 12, wherein the fluid comprises a comestible.

14. The method in accordance with claim 12, wherein the fluid comprises a pharmaceutical.

15. The method in accordance with claim 12, further comprising the step of introducing a growth, death and stasis factor into said simulated process prior to generating said statistical report.

16. The method in accordance with claim 12, further comprising the step of repeating the step of examining a portion of each selected simulated sample package for microorganisms a number of times prior to generating said statistical report.

17. The method in accordance with claim 12, further comprising the step of generating a probability of occurrence of packages with an integer number of organisms, given a specified average organism concentration during said simulated process.

* * * * *